United States Patent [19]
Emerson

[11] Patent Number: 5,628,228
[45] Date of Patent: May 13, 1997

[54] DEVICE FOR APPLYING PRESSURE TO A SWATCH FOR DETECTING DEBRIS ON ROLLS OF PAPER

[76] Inventor: Robert A. Emerson, 880 Poplar St., Bangor, Me. 04401

[21] Appl. No.: 531,385

[22] Filed: Sep. 21, 1995

[51] Int. Cl.$^6$ ............................................ G01L 5/04
[52] U.S. Cl. ................................................ 73/159
[58] Field of Search ............... 73/159, 160, 862.55, 73/862.581, 862.582, 862.583, 862.61; 116/321

[56] References Cited

U.S. PATENT DOCUMENTS

| | | | |
|---|---|---|---|
| 3,129,586 | 4/1964 | Allen et al. | 73/159 |
| 3,332,281 | 7/1967 | Spangler | 73/159 |
| 3,438,252 | 4/1969 | Whitehurst | 73/141 |
| 4,574,634 | 3/1986 | Pappano | 73/159 |
| 5,123,284 | 6/1992 | Edinburgh et al. | 73/159 |

*Primary Examiner*—George M. Dombroske
*Assistant Examiner*—William L. Oen
*Attorney, Agent, or Firm*—Core Flint; Gerald R. Boss

[57] ABSTRACT

A contamination gauge for paper manufacturing for detecting the debris on paper includes a hand-held housing having a gripping surface and a plunger carried axially by the housing having a pressure application surface disposed on one end of the plunger for applying a predetermined force. A force exerting element is carried within the interior of the housing for exerting the predetermined pressure when the housing is moved relative to the plunger. An indicator indicates when the housing has moved sufficiently for generating the predetermined amount of pressure. Also a method for testing the propensity of paper rolls to lint debris on printing machines is disclosed.

20 Claims, 3 Drawing Sheets

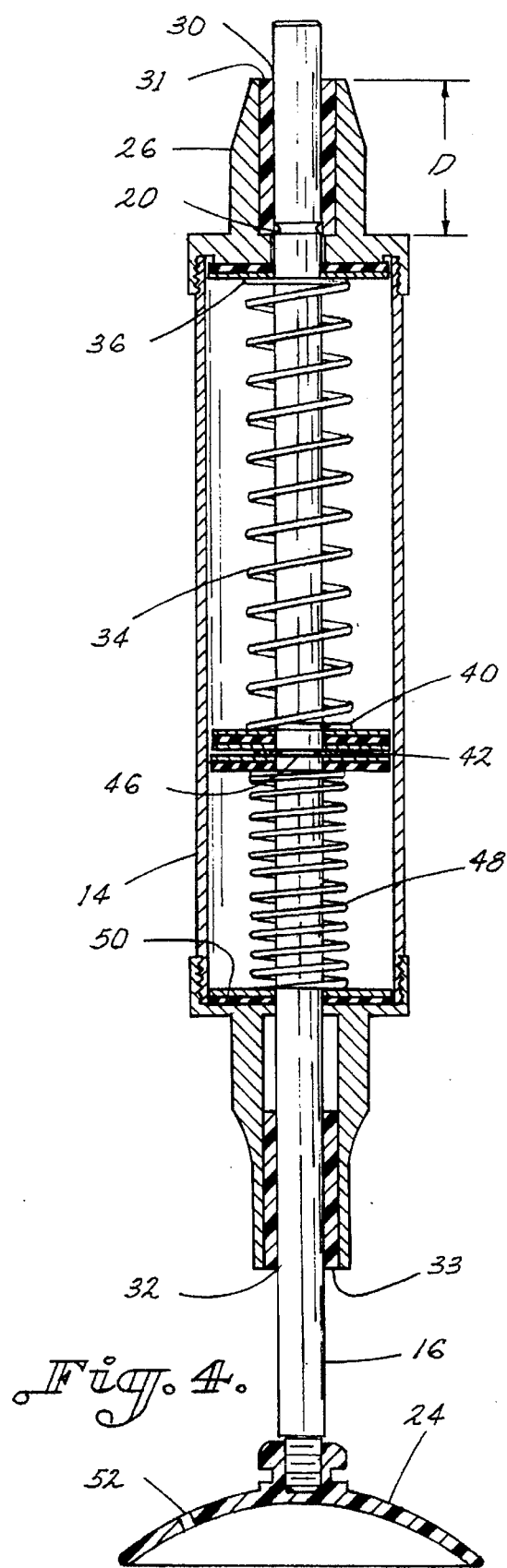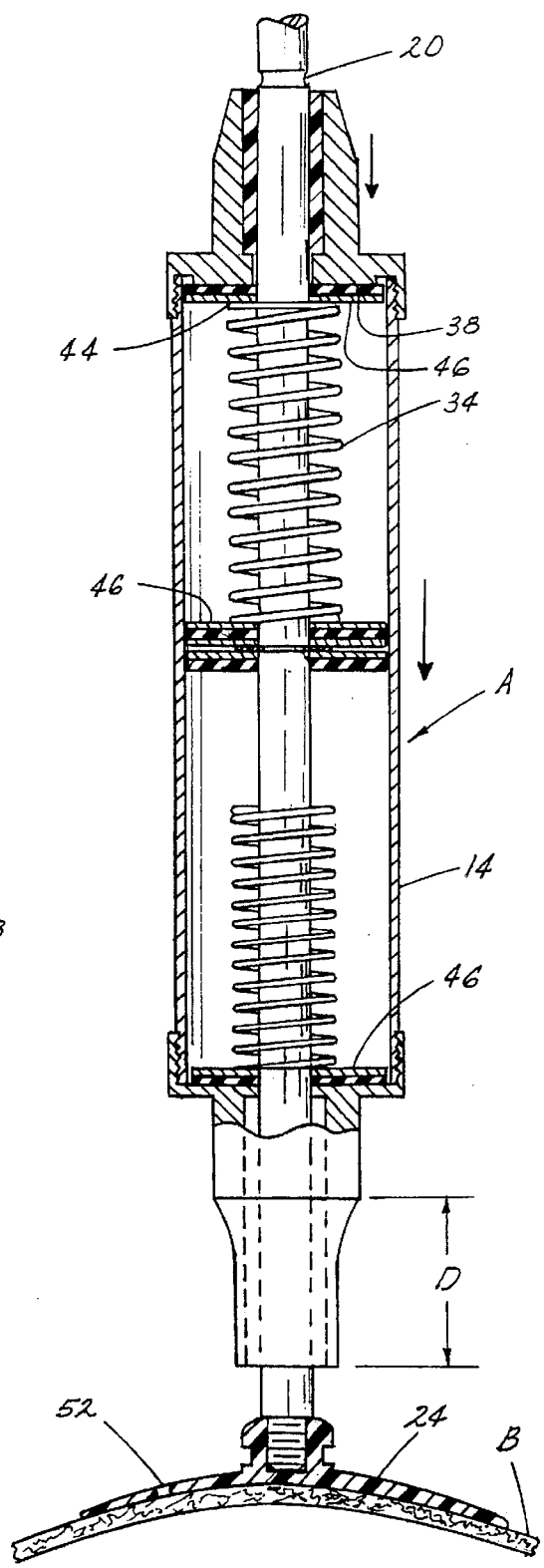

DEVICE FOR APPLYING PRESSURE TO A SWATCH FOR DETECTING DEBRIS ON ROLLS OF PAPER

BACKGROUND OF THE INVENTION

This invention relates to a pressure gauge in general, and more particularly to a device used in paper manufacturing, web press printing and paper coating which allows for a nondestructive, repeatable and consistent test for surface contamination.

The process of manufacturing paper involves combining various materials including wood pulp, filler, surface treatment chemicals, in an aqueous solution in a structure known as a head box. The aqueous solution is passed along a papermaking web as water is removed from the solution creating a solid paper film which may be further treated with coating chemicals or sizing chemicals in a structure known as the size press or coater. The film is eventually dried and wound on winders. In the newsprint and magazine industry, wounded rolls of paper for the printing process is then shipped to the printers for printing.

The problem arises when debris originating from the surface of the paper or paperboard contaminates the printing machines by depositing on the printing machines. Debris on the printing machines requires stopping the printing operation and cleaning the printing machines. The debris is caused by certain ones of the materials poorly binding to the surface of the sheet. These materials may include fiber and minerals which have been used as a low cost filler or fiber substitute and similar materials which were previously placed in the head box for providing the paper with strength and shininess. In printing operations, the debris causes problems such as contamination of the off-set print blanket, contamination of the printed image, and similar problems.

The contamination of printers is prevalent due to the increasing use of secondary pulp fibers and filler which are added to the pulp during papermaking to reduce cost and thus comply with contemporary marketing requirements. The secondary pulp fibers and filler are difficult to bind to the paper sheet surface typically causing higher levels of contamination problems during the printing operation.

Consequently, a need has arisen to reliably predict whether a sheet of paper or paperboard will deposit contamination either from fiber "linting" or mineral filler "dusting" during the printing operation. Generally contamination could only be evaluated during the performance of the printing operation which is generally too late and required the printing press to be shut down if contamination was too prevalent.

Previously, papermakers and printers, to detect the cleanliness of the paper sheet and thus the potential for contamination of the printing press, would apply a dark cloth to the surface of the sheet while the sheet was rotating on either the upwinder at the paper mill or the downwinder at the printer. By applying a cloth, by hand, to the sheet surface of the paper or paperboard, the propensity of the sheet to cause dusting or linting was roughly judged by observing the amount of debris accumulated on the cloth. The problem with this method is that the amount of pressure applied to the cloth and the time that the cloth is held against the sheet is inconsistent varying with the operator. This uncontrolled method of manually applying a sheet of dark cloth to the surface of the paper sheet produces inconsistent results depending on the operators and is inadequate.

Accordingly, it is an object of the present invention to provide a reliable method for testing the propensity of a roll of paper to cause dusting or linting during printing;

Also, it is an object of the present invention to provide a device that insures that a test cloth is pressed against a roll of paper at a controlled pressure for testing the propensity of the sheet to cause dusting or linting during printing;

Also, it is an object of the present invention to provide a dusting/surface contamination gauge which accurately and reliably indicates the application of a predetermined amount of pressure being applied to a test cloth;

Furthermore, it is an object of the present invention to provide a heavyduty dusting surface contamination gauge for industrial use.

SUMMARY OF THE INVENTION

The above objectives are accomplished according to the present invention by providing a portable pressure applicator for applying a predetermined amount of pressure to a sheet for contacting a roll of paper or paperboard while the roll is rotating on a roller for testing the debris on the roll. The applicator includes a hand-held housing having a gripping surface, an interior and a plunger channel. A plunger is carried axially within the housing interior and extends through the plunger channel. The housing is moveable relative to the plunger from a first position to a second position for exerting a predetermined pressure on the roll. A force exerting element is carried by the housing for exerting the predetermined pressure when the housing is moved to the second position. An indicator indicates when the force exerting element is exerting the predetermined pressure. A pressure application surface is carried by the plunger for transferring the force to the sheet.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein:

FIG. 4 illustrates a side sectional view of the device for applying pressure to a swatch according to the invention taken along line 4—4 of FIG. 3;

FIG. 4A illustrates a side sectional view of a device similar to FIG. 4 illustrating the device applying pressure to a swatch for testing the debris on a sheet of paper according to the invention;

DESCRIPTION OF A PREFERRED EMBODIMENT

Referring now in more detail to the drawings, the invention will now be described in more detail.

Figure 1:
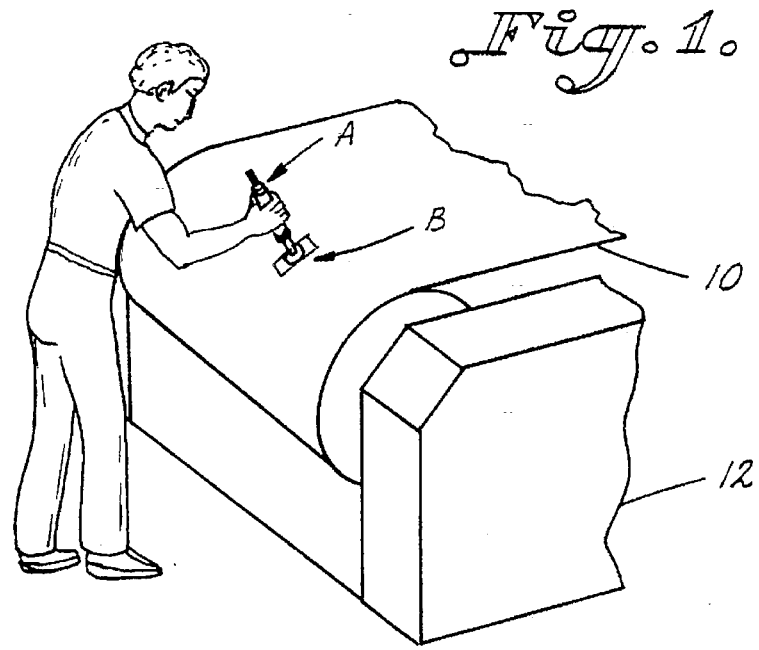
FIG. 1 illustrates an operator utilizing a device for applying pressure to a swatch for detecting debris on a roll of paper according to the invention.

As shown in FIG. 1, an operator utilizes pressure applicator A for applying pressure to sheet of material B for detecting debris on a finished sheet of paper or paperboard.

The operator places sheet B on paper or paperboard 10 and manipulates applicator A for applying a predetermined amount of pressure against sheet B firmly pressing sheet B against the surface of paper 10 as paper 10 is wound on a winder 12. The operator maintains the predetermined amount of pressure on sheet B for a predetermined amount of time enabling debris on sheet 10 to be accumulated on sheet B for later inspection in determining the amount of debris on sheet 10 and the propensity of debris to dislodge from sheet 10 which would possibly contaminate printing equipment.

As shown in FIGS. 2, 3, 4 and 5, applicator A includes housing 14 and plunger 16. Applicator A is portable and housing 14 includes a gripping surface. Plunger 16 carries pressure application surface 24. Force exerting element 34 is carried by housing 14 and applies pressure to plunger 16. Housing 14 is slidably mounted with respect to plunger 16 for activating force exerting element 34 for generating pressure which is transferred through plunger 16 to pressure application surface 24 for application to sheet B. In the preferred embodiment, sheet B is a black felt swatch. In order to consistently apply a predetermined amount of pressure, indicator 20 indicates when housing 14 has been moved a sufficient distance to generate the predetermined amount of pressure.

Figure 3:
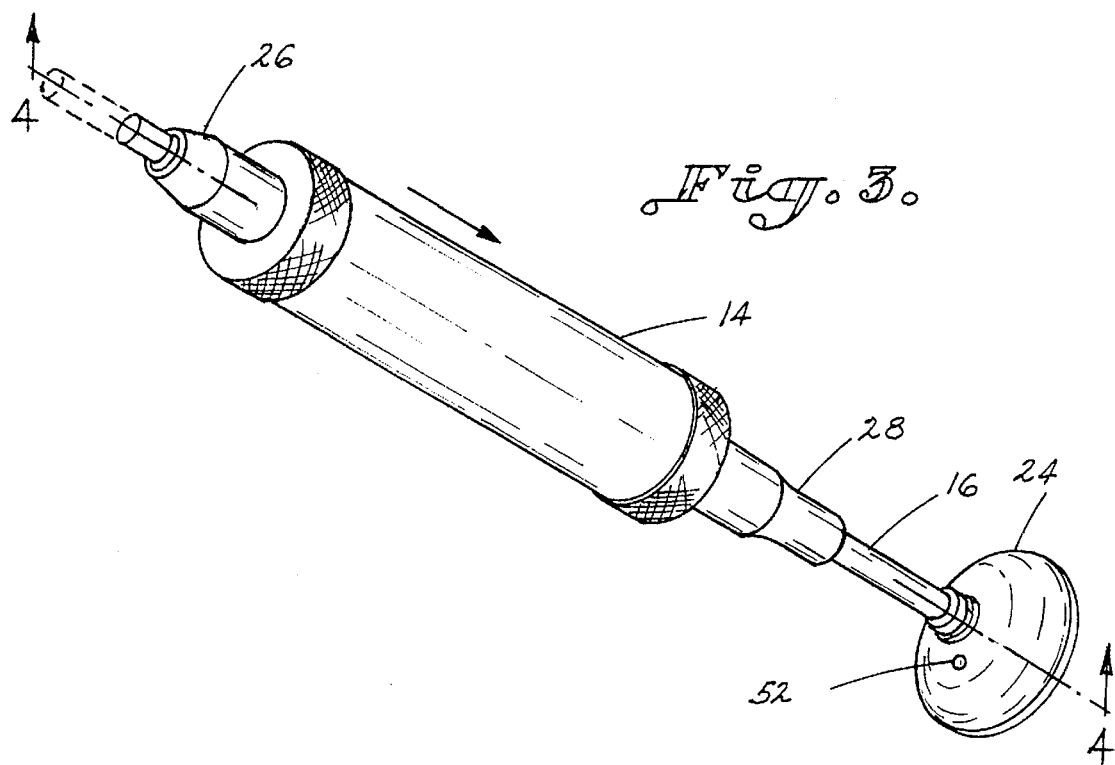
FIG. 3 illustrates a perspective view of the device for applying pressure to a swatch according to the invention.

As shown in FIG. 3, housing 14 has an initial resting position wherein housing 14 and plunger 16 are in an equilibrium state and no pressure is applied to pressure application surface 24 by force exerting element 34. Once housing 14 is moved downward to a second position, pressure will be applied to pressure application surface 24. Housing 14 will be moved downward until indicator 20 is exposed indicating that the predetermined pressure is being applied to sheet 10. Accordingly, when indicator 20 is exposed, housing 14 is in the preferred position for actuating force exerting element 34 applying the predetermined amount of pressure to pressure application surface 24. In the preferred embodiment indicator 20 is a groove formed within plunger 16 which is colored red for easy visibility.

In the preferred embodiment, plunger 16 is a cylindrical rod having a diameter of approximately a quarter of an inch. With the placement of pressure application surface 24 against sheet B on roll 10 as roll 10 winds, a downward force generally perpendicular to plunger 16 will be applied to plunger 16 by roll 10. Top support collar 26 and bottom support collar 28 provide plunger 16 with axial movement while restricting plunger 16 from bending. Top support collar 26 is carried by the top end of housing 14 and encircles plunger 16 radially supporting plunger 16. Top support collar 26 includes a top collar channel 30 permitting plunger 16 to be received through and extend beyond top support collar 26 when housing 14 is slid downward. Plastic tube 31 encircles plunger 16 within top collar channel 30, 26 for providing a smooth sliding surface enabling housing 14 to easily slide down plunger 16. Bottom support collar 28 is carried by the lower end of housing 14 to provide the lower end of plunger 16 with stability. Bottom support collar 28 includes bottom collar channel 32 permitting plunger 16 to be received through and extend beyond bottom support collar 28. Plastic tube 33 encircles plunger 16 within bottom collar channel 32 providing a smooth sliding surface enabling housing 14 to easily slide down the bottom portion of plunger 16. Housing 14 is preferably cylindrical for easily fitting with the operator's palm.

As shown in FIGS. 4 and 4A, force exerting element 34 includes a helical first spring. Force exerting element 34 has a first spring end 36 for being compressed by housing spring abutment 38 and a second spring end 40 for being compressed by plunger spring abutment 42. Housing 14 slides downward with respect to plunger 16 compressing the spring and generating the predetermined amount of pressure.

As shown in FIG. 4, housing spring abutment 38 is carried by housing 14 and transverses the interior of housing 14. Housing spring abutment 38 includes a central opening 44 enabling plunger 16 to pass through the upper portion of housing 14. In the preferred embodiment central opening 44 communicates with top collar channel 30. Housing spring abutment 38 may either be formed within housing 14 or top support collar 26 and compresses force exerting element 34 when housing 14 is moved downward on plunger 16. Plunger spring abutment 42 is carried by plunger 16 for engaging second end of force exerting element 34. In the preferred embodiment, groove 46 is formed around the circumference of plunger 16 and plunger spring abutment 42 is comprised of a lock ring which is maintained within groove 46. In order to facilitate the contact of housing spring abutment 38 and plunger spring abutment 42 with force exerting element 34, shims 46 are positioned between force exerting element 34 and housing spring abutment 38 and plunger spring abutment 42. Shims 46 consist of a rubber shim and a metallic shim.

As shown in FIG. 4, when housing 14 is in a first position and plunger 16 and housing 14 are at rest, no force is exerted by pressure application surface 24. In this first position, indicator 20 is enclosed by top support collar 26 and is not visible. As shown in FIG. 4A, in operation, when housing 14 is slid to a second position, force exerting element 34 is compressed between housing spring abutment 38 and plunger spring abutment 42. In this compressed state, force exerting element 34 generates a pressure which is transferred to plunger 16 through plunger spring abutment 42 resulting in the pressure being applied to sheet B through pressure application surface 24.

For consistently applying the same amount of pressure onto sheet B from applicator A, housing 14 is slid downward with respect to plunger 16 until indicator 20 is exposed just beyond the outer edge of top support collar 26 in this situation, the outer edge of top support collar defines a pointer pointing to said indicator for indicating when force exerting element 34 is exerting the required pressure. Indicator 20 is retained within housing 14 a predetermined distance, denoted by the letter D, so that when indicator 20 is exposed, housing 14 is compressing force exerting element 34 distance D resulting in force exerting element 34 generating a force equivalent to the desired predetermined pressure. For example, if the predetermined amount of pressure to be applied to sheet B is five pounds and force exerting element 34 has a spring constant of five pounds per inch, then indicator 20 would be distanced one inch from the end of housing 14 when housing 14 is in the first position. Housing 14 would be slid to the second position exposing indicator 20 just beyond the outer edge of top support collar 26 and compressing force exerting element 34 one inch thereby inducing force exerting element 34 to generate five pounds of pressure which is transferred to plunger application surface 24. To enable housing 14 to slide down plunger 16 to compress force exerting element 34 the required distance, plunger 16 and pressure application surface 24 extend a distance away from bottom support collar 28 greater than the compression distance D enabling housing 14 to slide down plunger 16 without bottom support collar 28 abutting plunger application surface 24.

Also shown in FIG. 4 a retainer 48 retains plunger 16 and housing 14 in equilibrium when housing 14 is in the first position. Retainer 48 is shown as a second spring. The second spring compensates for the distance that plunger spring abutment 42 is spaced from the lower end of housing 14 when force exerting element 34 is in its first position. Second spring abutment 50 abuts a second end of the second spring maintaining second spring between plunger spring abutment 42 for retaining plunger 16 in equilibrium with housing 14 when housing 14 is in the first position. In the preferred embodiment, second spring 48 has an elastic co-efficient less than the first spring. Retainer 48 may be a flange located within the interior of housing 14 for abutting plunger spring abutment 42.

Figure 2:
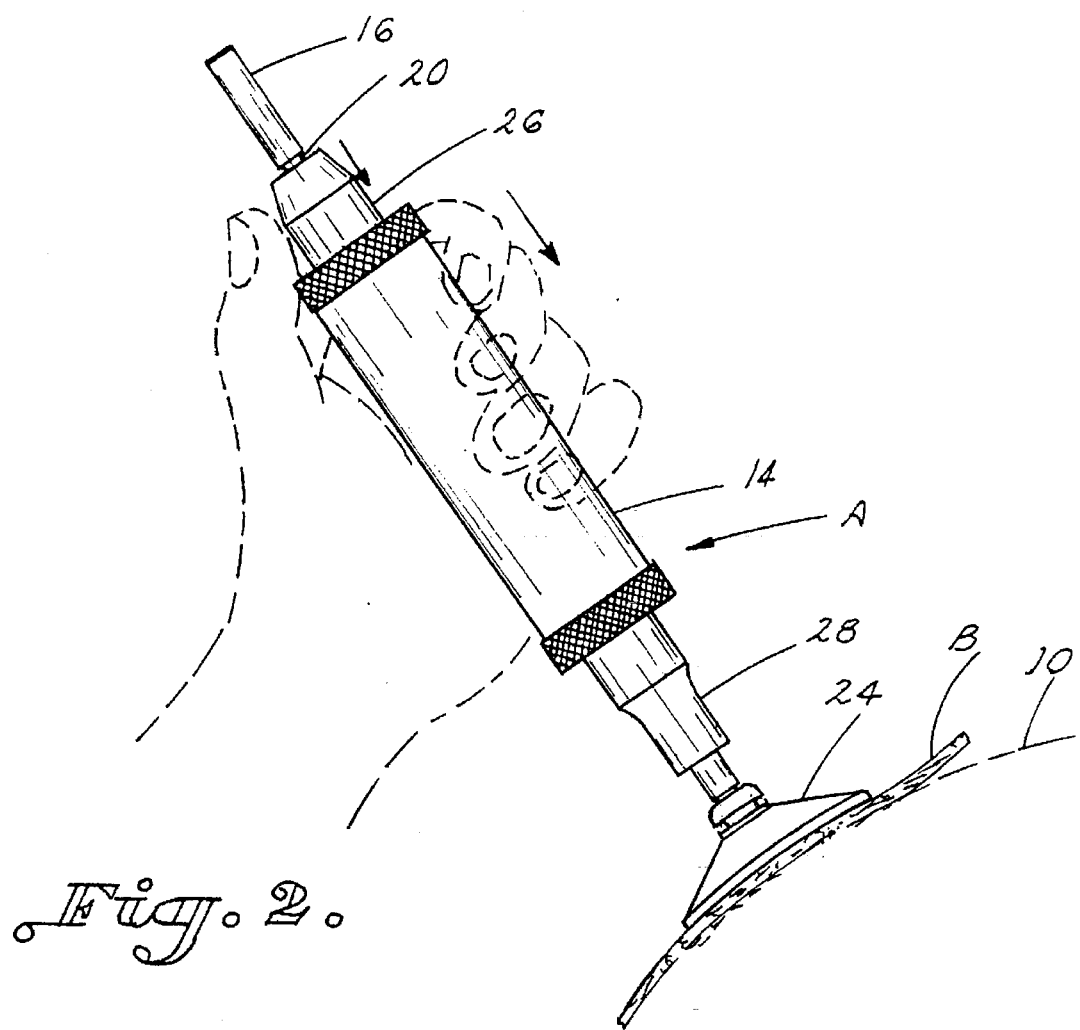
FIG. 2 illustrates a close up view of an operator applying pressure to a swatch utilizing a contamination gauge according to the invention.

As shown in FIGS. 2, 3 and 4, pressure application surface 24 is a deformable cup made from semi-resilient plastic. Pressure release aperture 52 is defined within the wall of the cup for permitting air to pass through the aperture enabling the cup to deform to the winding roll. This is necessary because the roll has an arced surface and the cup must be arced also for firmly placing the sheet against the roll.

Figure 5:
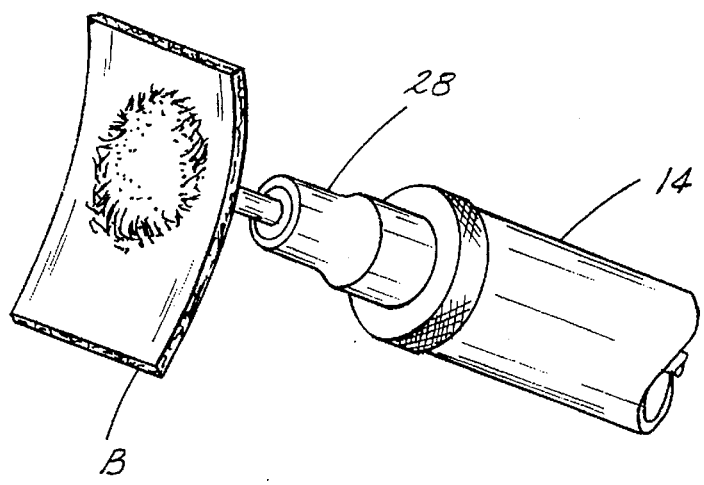
FIG. 5 illustrates a partial perspective view of debris accumulated on a swatch according to the invention.

As shown in FIG. 5, sheet B accumulates debris from the surface of the roll which will be examined for determining the quality of the sheet and if modifications to the manufacturing line must be made.

In operation, testing for the contamination of the paper would most normally be done at the wind up roller. If the testing was being conducted at the printers prior to inking this test would be at the unwind. Roll diameter is of no concern, as long as surface speed is constant. The operator holds the sheet onto the roll and applies the cup of the pressure applicator directly onto the other end of the sheet. The housing is slid downward until the indicator is exposed.

The only variable for testing the contamination is the length of paper to be tested. It has been found that for paper machines that run five hundred feet per minute or more a test of one thousand feet of paper is desired and for paper machines that run less than five hundred feet per minute a test of five hundred feet of paper is desired.

Thus it can be seen that an advantageous construction can be had for a device according to the invention where the amount of pressure to be applied to a test sheet for testing the debris on a roll of paper may be consistently applied in a manner that is not destructive to the roll of paper.

While a preferred embodiment of the invention has been described using specific terms, such description is for illustrative purposes only, and it is to be understood that changes and variations may be made without departing from the spirit or scope of the following claims.

What is claimed is:

1. A portable pressure applicator for applying a predetermined amount of pressure to a sheet for contacting a roll of paper or paperboard while said roll is rotating on a roller for testing the debris on said roll, said applicator comprising:

a hand-held housing having a gripping surface, an interior and a plunger channel;

a plunger carried axially within said housing interior extending through said plunger channel;

said housing being moveable relative to said plunger from a first position to a second position for exerting said predetermined pressure on said roll;

a force exerting element carried by said housing for exerting said predetermined pressure when said housing is moved to said second position;

an indicator communicating with said force exerting element for indicating when said force exerting element is exerting said predetermined pressure;

a pressure application surface carried by said plunger for transferring said force to said roll;

whereby a predetermined pressure may be applied to a roll by sliding said housing a sufficient distance for manipulating said force exerting element to generate a predetermined amount of pressure for application to said roll.

2. The pressure applicator of claim 1 wherein said indicator includes a mark disposed on said plunger initially enclosed by said housing when said housing is in said first position and said mark being visible when said housing is moved to said force exerting position for indicating that said predetermined pressure is exerted by said force exerting element.

3. The pressure applicator of claim 1 wherein said pressure application surface includes a deformable resilient cup which deforms to the surface of said roll.

4. The pressure applicator of claim 3 including a pressure release defined within said resilient cup enabling air to pass through for enabling said cup to deform to the surface of said roll.

5. The pressure applicator of claim 1 wherein said housing is slidable relative to said plunger for sliding from said first position to said second position for exerting said predetermined pressure on said roll.

6. A portable pressure applicator for applying a predetermined amount of pressure to a sheet for contacting a roll of paper or paperboard while said roll is rotating on a roller for testing the debris on said roll, said applicator comprising:

a hand-held housing having a gripping surface, an interior and a plunger channel;

a plunger carried axially within said housing interior extending through said plunger channel;

said housing being moveable relative to said plunger from a first position to a second position for exerting said predetermined pressure on said roll;

a housing spring abutment carried by a first end of said housing;

a plunger spring abutment carried by said plunger;

a first spring carried by said plunger between said housing spring abutment and said plunger spring abutment, said spring having a compressed position generating a spring pressure generally equal to said predetermined pressure when said housing is moved to said second pressure exerting position;

an indicator carried by said plunger indicating when said spring has been compressed for generating said predetermined pressure;

a pressure application surface carried by said plunger for transferring said pressure to said target;

whereby a predetermined pressure may be applied to a roll by sliding said housing a sufficient distance along said plunger compressing said spring a sufficient distance to generate a predetermined amount of pressure for application to said roll.

7. The pressure applicator of claim 6 wherein said indicator includes a mark disposed on said plunger and said housing carries a pointer pointing to said indicator when said housing is moved to said second pressure exerting position for indicating when said spring has been sufficiently compressed for generating said predetermined pressure.

8. The pressure applicator of claim 7 including a first support collar carried by and extending from a first end of said housing, said first support collar defining a first collar channel for axially receiving and supporting said plunger, said first support collar having an end wall defining said pointer.

9. The pressure applicator of claim 6 including a second support collar carried by and extending from a second end of said housing, said second support collar defining a second collar channel for axially receiving and supporting said plunger.

10. The pressure applicator of claim 9 including a second spring abutment carried by said second end of said housing, and also including a second spring intermediarily disposed between said plunger spring abutment and said second spring abutment, said second spring in combination with said first spring maintaining said housing and plunger at equilibrium.

11. The pressure applicator of claim 10 wherein said first spring has an elastic coefficient greater than said second spring.

12. The pressure applicator of claim 6 wherein said first spring has an elastic coefficient sufficient to generate a spring pressure generally equivalent to five pounds.

13. The pressure applicator of claim 6 including a deformable concave cup defining said pressure application surface, said cup for deforming to the surface of said roll for transferring said plunger pressure to said target.

14. The pressure applicator of claim 13 wherein said concave cup includes a pressure release aperture defined within said cup for enabling air to pass from the interior of said cup to the exterior of said cup when said cup is pressed against said roll.

15. A method for testing the debris on a roll of paper while said roll is rotating on a roller, said method comprising:

providing a pressure applicator designed to apply a predetermined amount of pressure;

providing a colored sheet of fabric having a rough surface;

positioning said colored sheet of fabric against the surface of said roll;

positioning said pressure applicator against the surface of said sheet of fabric;

applying said predetermined amount of pressure from said pressure applicator to said sheet of fabric;

maintaining said application of said predetermined amount of pressure on said sheet for a predetermined period of time for collecting debris from said roll;

removing said pressure from said sheet;

removing said sheet from said roll.

16. The method of claim 15 including comparing said sheet after removal from said roll to a control sheet for determining the amount of debris on said roll.

17. The method of claim 15 including providing said pressure applicator in the form of a hand-held housing having an axial plunger extending through at least one end of said housing with a pressure application surface which applies a force induced by movement of said housing relative to said plunger which is indicated by an indicator.

18. The method of claim 15 including maintaining said application of said predetermined pressure on said sheet for a predetermined time to enable a predetermined length of roll to be tested for determining the contamination potential of said roll.

19. The method of claim 18 wherein said predetermined length of roll is five hundred feet for paper machines that run less than five hundred feet per minute.

20. The method of claim 18 wherein said predetermined length of roll is one thousand feet for paper machines that run faster than five hundred feet per minute.

* * * * *